(12) United States Patent
Akisada et al.

(10) Patent No.: US 8,109,452 B2
(45) Date of Patent: Feb. 7, 2012

(54) ELECTROSTATIC ATOMIZER FOR USE IN A MOTOR VEHICLE

(75) Inventors: Shousuke Akisada, Hirakata (JP); Takeshi Yano, Kyoto (JP); Akihide Sugawa, Hikone (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 145 days.

(21) Appl. No.: 12/320,025

(22) Filed: Jan. 15, 2009

(65) Prior Publication Data

US 2009/0179092 A1    Jul. 16, 2009

(30) Foreign Application Priority Data

Jan. 15, 2008    (JP) .................... 2008-006114

(51) Int. Cl.
*B05B 5/04* (2006.01)
*B05B 5/035* (2006.01)
*B05B 5/025* (2006.01)
*B05B 5/00* (2006.01)

(52) U.S. Cl. ........... 239/698; 239/67; 239/690; 239/697

(58) Field of Classification Search .................. 239/690, 239/690.1, 695–698, 704, 706, 707, 67, 69, 239/70; 454/110, 152, 154, 155, 157
See application file for complete search history.

(56) References Cited

U.S. PATENT DOCUMENTS

| 4,881,456 A | 11/1989 | Yasuda et al. |
| 2003/0186644 A1 | 10/2003 | Abe et al. |

FOREIGN PATENT DOCUMENTS

| JP | 2005-059763 | 3/2005 |
| JP | 2006-111227 | 4/2006 |
| JP | 2006-151046 | 6/2006 |

*Primary Examiner* — Darren W Gorman
(74) *Attorney, Agent, or Firm* — Bacon & Thomas, PLLC

(57) ABSTRACT

An electrostatic atomizer, for use in a motor vehicle, includes a discharge electrode, a water supply unit for cooling the discharge electrode to generate water condensed on the discharge electrode, and a high voltage applying unit for applying a high voltage to the water on the discharge electrode to electrostatically atomize the water. The electrostatic atomizer is arranged in a ceiling of the motor vehicle. The electrostatic atomizer further includes an ejection portion provided in the ceiling of the motor vehicle for ejecting electrically-charged water particles generated by electrostatic atomization and an ejection direction changing unit provided in the ejection portion for changing an ejection direction of the electrically-charged water particles.

11 Claims, 10 Drawing Sheets

ELECTROSTATIC ATOMIZER FOR USE IN A MOTOR VEHICLE

FIELD OF THE INVENTION

The present invention relates to an electrostatic atomizer for use in a motor vehicle.

BACKGROUND OF THE INVENTION

In motor vehicles such as a passenger car and the like, a vehicle room is formed of a closed space and therefore may be filled with the smell of tobacco or other odors. In view of this, various kinds of filter-type air purifiers have become available. However, the air purifiers are incapable of removing the odor components adhering to a wall surface or other parts of the vehicle room.

In recent years, attention is paid to an electrostatic atomizer that generates electrically-charged water particles of nanometer size (nano-size mist) by atomizing water. The nano-size mist generated in the electrostatic atomizer contains radicals such as superoxide radicals or hydroxyl radicals and provides an effect of deodorization, an effect of controlling viruses or funguses and an effect of inactivating allergenic substances. Therefore, if the nano-size mist is blown into a vehicle room, it is possible to remove the odor components present in an air within the vehicle room or adhering to wall surfaces of the vehicle room or vehicle seats. It is also possible to control allergens such as the bodies of ticks adhering to seats, floor carpets or cushions and the pollen brought into the vehicle room while opening a door or window of the vehicle or carried into the vehicle room with the clothes of a passenger. Japanese Patent Laid-open Publication No. 2006-151046 (JP2006-151046A) discloses an electrostatic atomizer for use in a motor vehicle in which nano-size mist is blown by the wind of an air conditioner to be sprayed into a vehicle room.

In case where the nano-size mist is blown by the air-conditioning wind and sprayed into the vehicle room from a front ejection port of the air conditioner as in the conventional example disclosed in JP2006-151046A, a discharge electrode is cooled to have the moisture present in an air condensed. The condensate water thus obtained is electrostatically atomized to generate electrically-charged water particles of nanometer size (nano-size mist). However, this atomizing method is fully governed by the change in temperature and humidity of the air-conditioning wind, which makes it impossible to generate the nano-size mist in a stable manner. In addition, since the nano-size mist is blown by the air-conditioning wind and sprayed from the front ejection port of the air conditioner, it is sometimes the case that the nano-size mist impinges against front seats and fails to smoothly reach the rear space of the vehicle room.

In the conventional example disclosed in JP2006-151046A, although the nano-size mist is sprayed from the front ejection port of the air conditioner to be adhered to the front body surface of a vehicle occupant, it is impossible to have the nano-size mist adhere to the hair of the vehicle occupant in an efficient manner.

SUMMARY OF THE INVENTION

The present invention provides an electrostatic atomizer for use in a motor vehicle, which is capable of generating nano-size mist, diffusing the same inside a vehicle room, removing odors and inactivating allergens within the vehicle room, effectively spraying the nano-size mist on the hair or the skin of a vehicle occupant and naturally caring for the hair or the skin of the vehicle occupant while the vehicle occupant stays in the vehicle room.

In accordance with an aspect of the present invention, there is provided an electrostatic atomizer for use in a motor vehicle, including: a discharge electrode; a water supply unit for cooling the discharge electrode to generate water condensed on the discharge electrode; and a high voltage applying unit for applying a high voltage to the water on the discharge electrode to electrostatically atomize the water, wherein the electrostatic atomizer is arranged in a ceiling of the motor vehicle.

With the construction noted above, the electrically-charged water particles of nanometer size (nano-size mist) generated in the electrostatic atomizer is sprayed from the ceiling of a motor vehicle. Therefore, it is possible to stably generate the nano-size mist, despite the fact that water is supplied to the discharge electrode by cooling the latter and inducing condensate water on the surface of the discharge electrode. This is because the change in temperature and humidity caused by the ejection of an air-conditioning wind is kept small as compared to the conventional example in which an electrostatic atomizer is arranged in or around the front ejection port of an air conditioner of the motor vehicle. Owing to the fact that the nano-size mist is sprayed from the ceiling of the motor vehicle, it is possible to efficiently diffuse the nano-size mist throughout the vehicle room and to remove the odor components present in an air within the vehicle room or adhering to wall surfaces of the vehicle room or seats. It is also possible to control allergens such as the bodies of ticks adhering to seats, floor carpets or cushions and the pollen brought into the vehicle room while opening a door or window of the vehicle or carried into the vehicle room with the clothes of a passenger. Furthermore, the nano-size mist can be effectively sprayed on the head of the vehicle occupant from above. This moisturizes the hair and keeps the same from over-drying, thus imparting a treatment effect to the hair. Since the nano-size mist is weakly acidic, it is possible to make the hair weakly acidic and soft. Further, the nano-size mist is infiltrated into the skin to keep the same wet and moisturized.

Preferably, the electrostatic atomizer is arranged in the ceiling of the motor vehicle at a position above a seat.

With the construction noted above, it is possible to effectively spray the nano-size mist from above toward the seats or the persons sitting on the seats. In particular, it is possible to effectively spray the nano-size mist from above toward the hair of the persons sitting on the seats.

Preferably, the electrostatic atomizer further includes an ejection portion provided in the ceiling of the motor vehicle for ejecting electrically-charged water particles generated by electrostatic atomization and an ejection direction changing unit provided in the ejection portion for changing an ejection direction of the electrically-charged water particles.

With the construction noted above, it becomes possible to concentratedly spray the nano-size mist on a particular point within the vehicle room by changing the direction in which the nano-size mist is ejected from the ejection portion provided in the ceiling.

Preferably, the electrostatic atomizer further includes a human body detection sensor for detecting a person, and the ejection direction changing unit is designed to direct the electrically-charged water particles toward the person detected by the human body detection sensor.

With the construction noted above, it is possible to effectively spray the electrically-charged water particles toward the persons sitting on the seats.

In accordance with the present invention, the electrostatic atomizer is arranged in the ceiling as set forth above. Therefore, it is possible to stably generate the nano-size mist by reducing the influence on the nano-size mist of the change in temperature and humidity caused by the ejection of the air-conditioning wind. The spray of the nano-size mist from the ceiling makes it possible to efficiently diffuse the nano-size mist throughout the vehicle room. This allows the nano-size mist to effectively reach the odor components adhering to the seats or the allergens permeating into the seats, thereby removing or inactivating the odor components and the allergens. In particular, the nano-size mist can be effectively sprayed on the head of the vehicle occupant from above. This moisturizes the hair and keeps the same from over-drying, thus imparting a treatment effect to the hair. Since the nano-size mist is weakly acidic, it is possible to make the hair weakly acidic and soft. Further, the nano-size mist is infiltrated into the skin to keep the same wet and moisturized. Thus, the hair care or the skin care is automatically and effectively carried out if the vehicle occupant merely sits on the seat.

BRIEF DESCRIPTION OF THE DRAWINGS

The above and other objects and features of the present invention will become apparent from the following description of embodiments, given in conjunction with the accompanying drawings, in which:

FIG. 1 is a schematic configuration view showing a motor vehicle in which an electrostatic atomizer is arranged in a generally central region of a ceiling of the vehicle;

FIGS. 2A and 2B are schematic configuration views showing a motor vehicle in which the electrostatic atomizer is arranged in a front region of a ceiling of the vehicle and a motor vehicle in which the electrostatic atomizer is arranged in a rear region of a ceiling of the vehicle, respectively;

FIG. 3 is a schematic configuration view illustrating the electrostatic atomizer;

FIGS. 4A and 4B are explanatory views illustrating different instances in which the ejection direction of nano-size mist is changed by an ejection direction changing unit provided in the ejection portion of a ceiling of the vehicle;

FIG. 5 is a control block diagram illustrating an electrostatic atomizer in which a human body detection sensor is employed to change the ejection direction of nano-size mist;

FIG. 6 is a schematic configuration view showing a motor vehicle in which the electrostatic atomizer having the human body detection sensor is installed in a generally central region of a ceiling of the vehicle;

FIGS. 7A and 7B are schematic configuration views showing a motor vehicle in which the electrostatic atomizer having the human body detection sensor is installed in a front region of a ceiling of the vehicle and a motor vehicle in which the electrostatic atomizer having the human body detection sensor is installed in a rear region of a ceiling of the vehicle, respectively;

FIG. 8 is a control block diagram illustrating the relationship of the electrostatic atomizer with respect to a battery and an ignition key switch;

FIG. 9 is a control block diagram illustrating one example of a keyless remote entry system associated with the electrostatic atomizer;

FIG. 10 is a time chart illustrating the operation of the electrostatic atomizer; and FIG. 11 is a control block diagram illustrating another example of a keyless remote entry system associated with the electrostatic atomizer.

DETAILED DESCRIPTION OF THE EMBODIMENTS

Hereinafter, embodiments of the present invention will be described in detail with reference to the accompanying drawings.

FIG. 3 shows an atomizer unit 1 of an electrostatic atomizer for generating electrically-charged water particles of nanometer size (nano-size mist). The atomizer unit 1 includes a discharge electrode 11 surrounded by an hollow body 16 made of an insulating material, a ring-shaped counter electrode 12 arranged in the tip end opening of the hollow body 16, a cooler unit 13 for cooling the discharge electrode 11 to have the moisture present in the air condensed on the discharge electrode 11 and a high voltage power source unit 15 for applying a high voltage to between the discharge electrode 11 and the counter electrode 12. The cooler unit 13 is formed of a Peltier element. The discharge electrode 11 is thermally connected to the cooling side of the cooler unit 13. The cooler unit 13 is provided with radiator fins 14 on the radiating side thereof.

The atomizer unit 1 further includes a motor fan (not shown) for blowing a cooling air toward the radiator fins 14. A part of the air sent from the motor fan enters the hollow body 16 through the side openings of the latter and then comes out through the tip end opening, i.e., an outlet port 17.

In the atomizer unit 1, condensate water is generated on the discharge electrode 11 by cooling the discharge electrode 11 with the cooler unit 13 and condensing the moisture present in the air. This means that the cooler unit 13 constitutes a moisture supply unit for supplying moisture to the discharge electrode 11. If a high voltage is applied to between the discharge electrode 11 and the counter electrode 12 in a state that the condensate water adheres to the discharge electrode 11, the condensate water is gathered at the tip end of the discharge electrode 11 and is converted to a nano-size mist M through the Rayleigh scattering repeatedly performed by the electric discharge occurring between the discharge electrode 11 and the counter electrode 12. The nano-size mist M is blown by the wind fed from the motor fan and is ejected to the outside through the outlet port 17. The atomizer unit 1 includes a discharge voltage detection circuit, a discharge current detection circuit and a control circuit that controls the generation quantity of condensate water by adjusting the cooling degree of the cooler unit 13 based on the discharge voltage and the discharge current detected by the discharge voltage detection circuit and discharge current detection circuit. The control circuit ensures that a moderate amount of condensate water is always gathered on the discharge electrode 11, thereby reliably generating the nano-size mist M regardless of the temperature and humidity.

The atomizer unit 1 configured as above is installed in the ceiling 20 of a vehicle room 21 of a motor vehicle 2 as shown in FIGS. 1, 2A and 2B so that it can supply the nano-size mist M into the vehicle room 21 from the ceiling 20.

As shown in FIG. 1, the atomizer unit 1 is arranged in, e.g., a generally central region of the ceiling 20 that corresponds to the generally center position between front and rear seats 22 and also to the transverse center position of the motor vehicle 2. Alternatively, the atomizer unit 1 may be arranged above one of the front and rear seats 22. In other words, the atomizer unit 1 may be arranged in the ceiling 20 either above the front seat 22 as illustrated in FIG. 2A or above the rear seat 22 as illustrated in FIG. 2B. Furthermore, the atomizer unit 1 may be arranged only in the ceiling 20 just above the driver's seat or may be arranged in different regions of the ceiling 20 above the respective seats 22.

If the atomizer unit 1 is arranged in the ceiling 20 of the motor vehicle 2 as set forth above and if the nano-size mist M is sprayed downwards from an ejection portion 30 provided in the ceiling 20, it is possible to efficiently diffuse the nano-size mist throughout the vehicle room 21 and to remove the odor components present in the air within the vehicle room 21 or adhering to the wall surfaces of the vehicle room 21 or the seats 22. It is also possible to control allergens such as the bodies of ticks adhering to the seats 22, floor carpets or cushions and the pollen brought into the vehicle room 21 while opening a door or window of the vehicle or carried into the vehicle room 21 with the clothes of a passenger.

Moreover, since the nano-size mist M is sprayed from the ceiling 20 of the motor vehicle 2, it is possible to effectively spray the nano-size mist M toward the head of a vehicle occupant from above.

Owing to the fact that the nano-size mist M is sprayed from above toward the person sitting on the seat 22 of the motor vehicle 2, the hair of the vehicle occupant is naturally supplied with moisture if the vehicle occupant merely sits on the seat 22. This prevents the hair from over-drying. Furthermore, the nano-size mist M generated by electrostatic atomization imparts a treatment effect to the surface of hair, thus keeping the hair glossy and wet. In addition, the nano-size mist M is weakly acidic and is effective in making the hair soft. Further, the nano-size mist M is infiltrated into the skin to keep the same wet and moisturized. Thus, the hair care or the skin care is unconsciously and naturally carried out if the vehicle occupant merely sits on the seat 22 of the motor vehicle 2.

Figure 1:
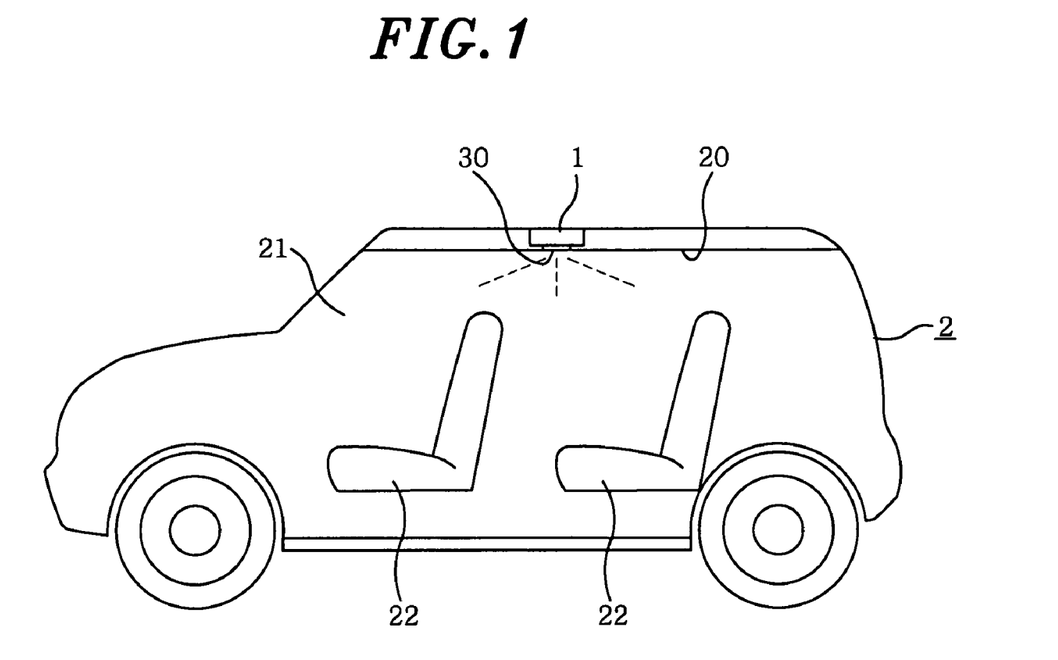

In this regard, if the atomizer unit 1 is arranged in the generally central region of the ceiling 20 that corresponds to the generally center position between the front and rear seats 22 and also to the transverse center position of the motor vehicle 2 as shown in FIG. 1, it becomes possible to more efficiently diffuse the nano-size mist M toward each and every corner of the vehicle room 21 when the nano-size mist M is sprayed downwards from the ceiling 20.

Figure 2A:
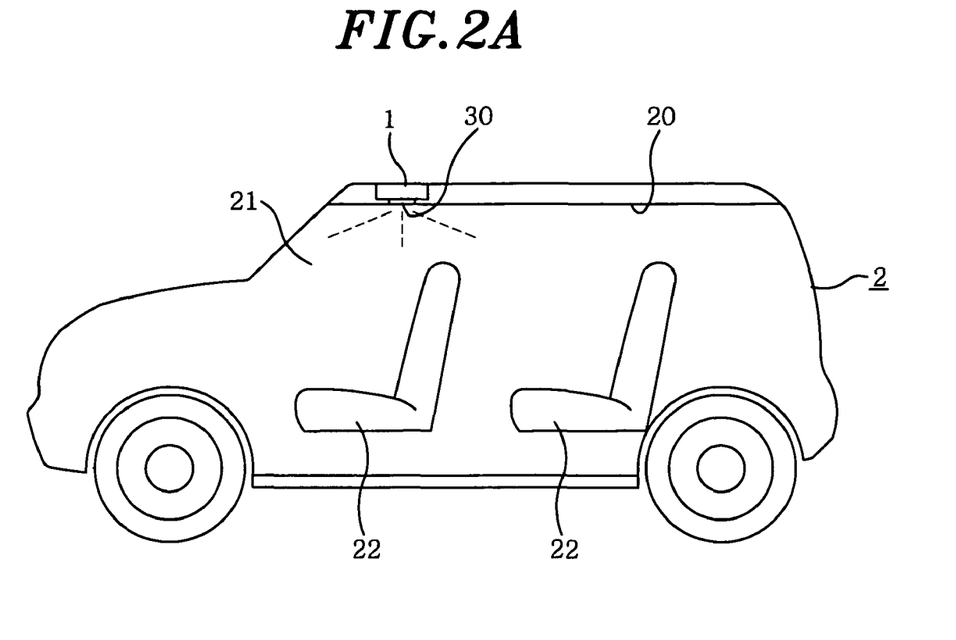
Figure 2B:
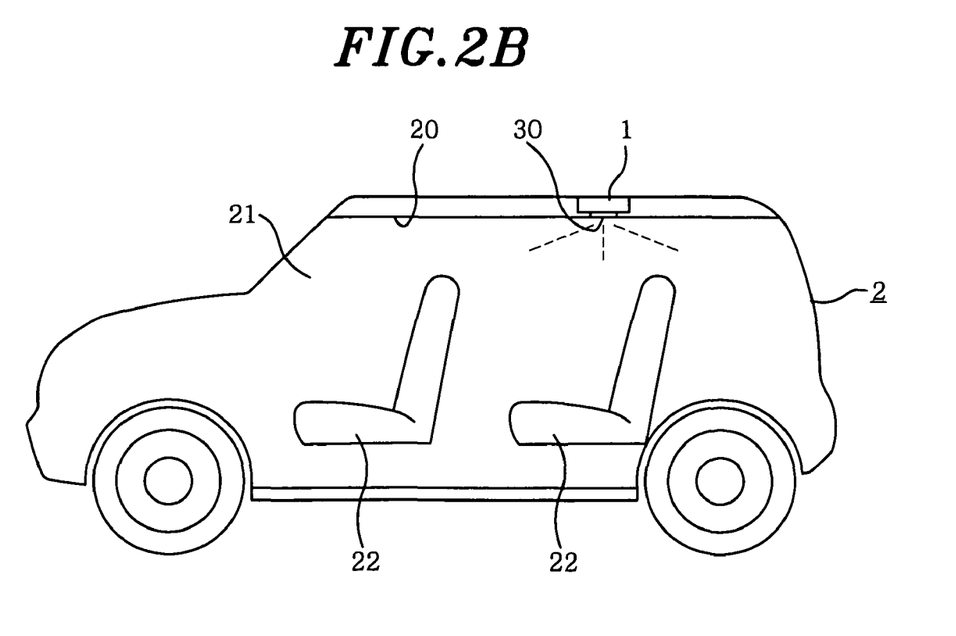
Figure 3:
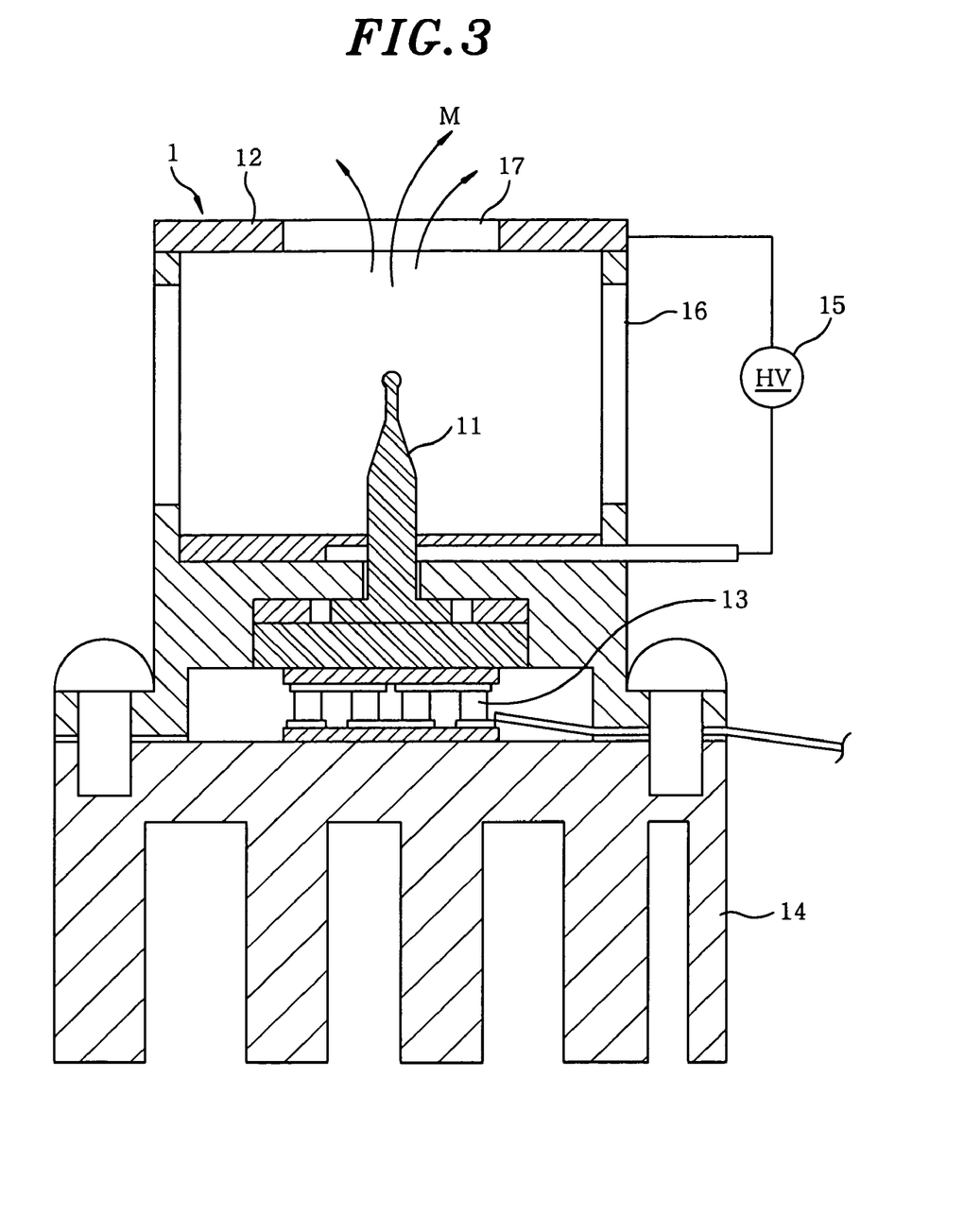

Even when the atomizer unit 1 is arranged in the ceiling 20 of the motor vehicle 2 above the seats 22 as illustrated in FIGS. 2A and 2B, since the nano-size mist M is sprayed downwards from the ceiling 20, it is possible to diffuse the nano-size mist M throughout the vehicle room 21 and to spray an increased amount of nano-size mist M toward the seats 22 positioned just below the atomizer unit 1. In case where no person sits on the seat 22 positioned just below the atomizer unit 1, it is possible to more concentratedly spray the nano-size mist M on the unoccupied seat 22 than on other portions within the vehicle room 21, thereby removing the odor components adhering to the seat 22. When the seat 22 is occupied by a person, it is possible to concentratedly spray the nano-size mist M toward the person, particularly the head of the person, from above. This makes it possible to effectively carry out the hair care or the face care by spraying the nano-size mist M on the hair or the face of the person sitting on the seat 22.

Figure 4A:
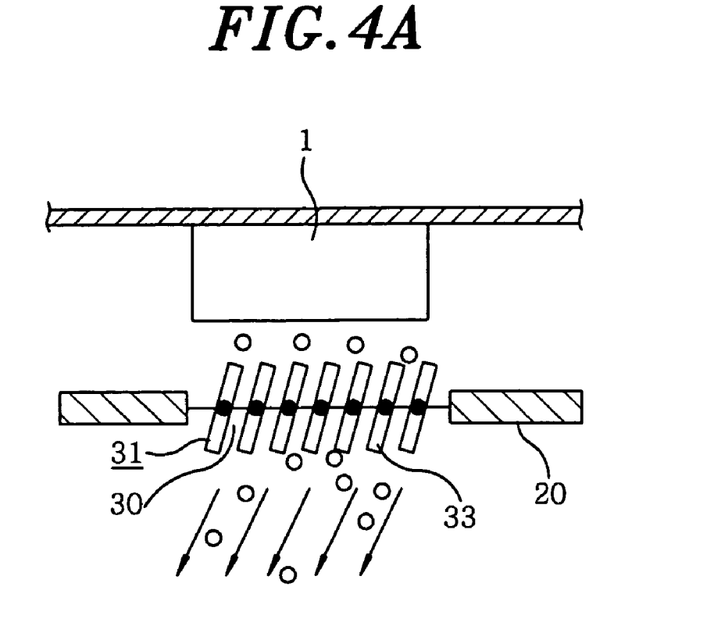
Figure 4B:
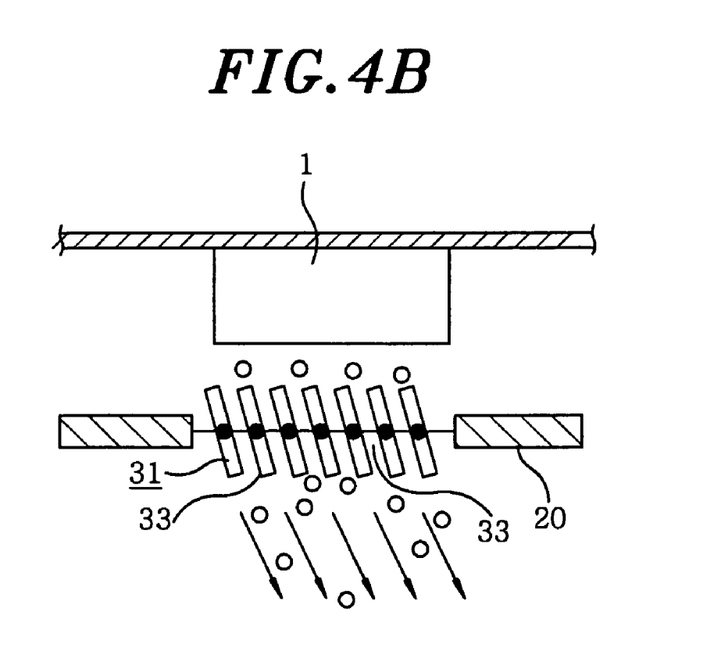

In any of the instances set forth above, the electrostatic atomizer may include an ejection direction changing unit 31 for changing the ejection direction of the nano-size mist M. As shown in FIGS. 4A and 4B, the ejection direction changing unit 31 is arranged in the ejection portion 30 through which the nano-size mist M generated in the atomizer unit 1 is ejected from the ceiling 20 into the vehicle room 21. In the example shown in FIGS. 4A and 4B, the ejection direction changing unit 31 is constructed from a louver 33 rotatably attached to the ejection portion 30. As can be seen in FIGS. 4A and 4B, the louver 33 is rotated to change its orientation, namely the ejection direction of the nano-size mist M. The ejection direction changing unit 31 may change the ejection direction of the nano-size mist M manually or automatically using a drive unit such as an electric motor or the like.

In case where the ejection direction of the nano-size mist M is automatically changed using the drive unit such as the electric motor, the electrostatic atomizer may include a human body detection sensor 32 that detects a vehicle occupant staying within the vehicle room 21 of the motor vehicle 2. The human body detection sensor 32 generates a detection signal when it detects a person sitting on any one of the seats 22. Responsive to the detection signal, the ejection direction changing unit 31 is automatically driven to ensure that the nano-size mist M is ejected from the ejection portion 30 toward the person detected.

Figure 6:
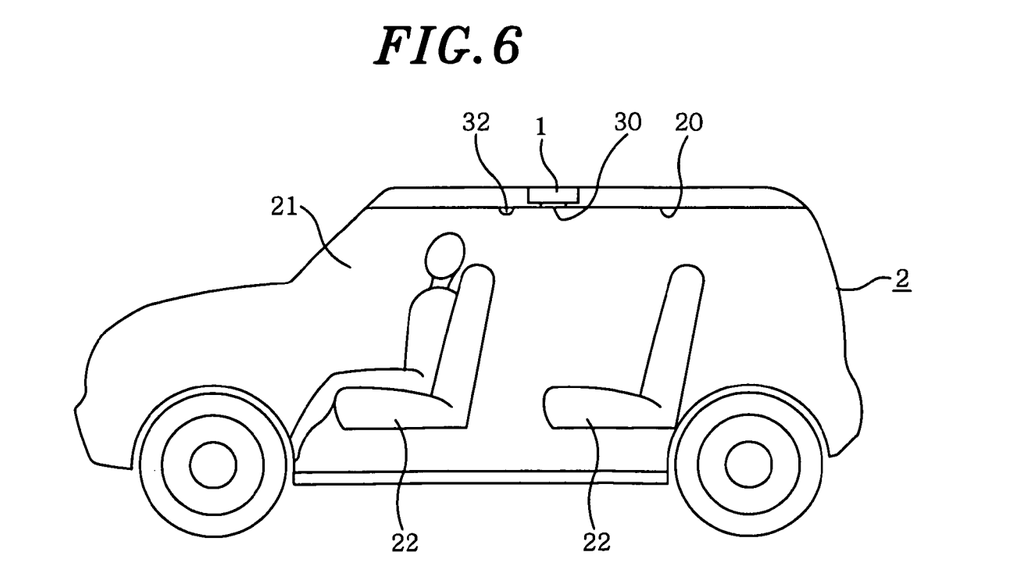
Figure 7A:
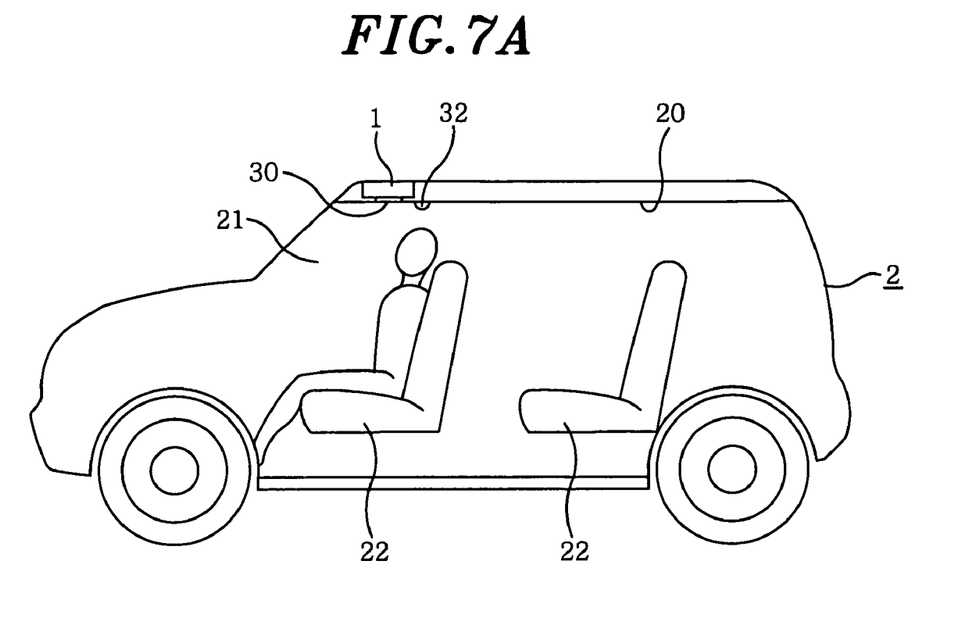
Figure 7B:
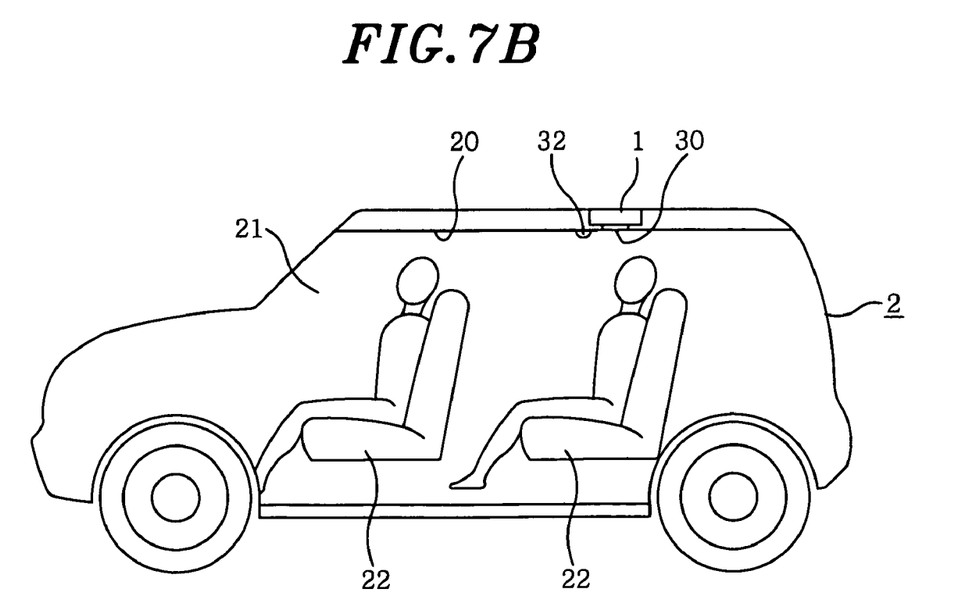

In an instance where the atomizer unit 1 is arranged in the generally central region of the ceiling 20 as shown in FIG. 6 or an instance where the atomizer unit 1 is arranged in the front or rear region of the ceiling 20 as shown in FIGS. 7A and 7B, the human body detection sensor 32 detects a person sitting on the driver's seat and enables the ejection direction changing unit 31 to be automatically driven so that the nano-size mist M can be sprayed from the ceiling 20 toward the driver's seat.

If the driver's seat and one or more of the seats 22 other than the driver's seat are occupied by persons, the human body detection sensor 32 detects the persons sitting on those seats. In this case, the ejection direction changing unit 31 is driven to change the ejection direction of the nano-size mist M in such a way that the nano-size mist M is sprayed toward the seats occupied by the persons one after another. In other words, if the human body detection sensor 32 detects persons sitting on seats A and B, the ejection direction changing unit 31 is driven to initially eject the nano-size mist M toward the seat A. After the nano-size mist M is ejected toward the seat A for a specified period of time, the ejection direction changing unit 31 is then operated to eject the nano-size mist M toward the seat B. In this way, the nano-size mist M is sprayed toward the seats A and B in turn. Then, the ejection direction changing unit 31 is restored to its initial state to spray the nano-size mist M toward the seat A again. The ejection direction changing unit 31 is controlled to repeat the above-noted procedure.

Figure 5:
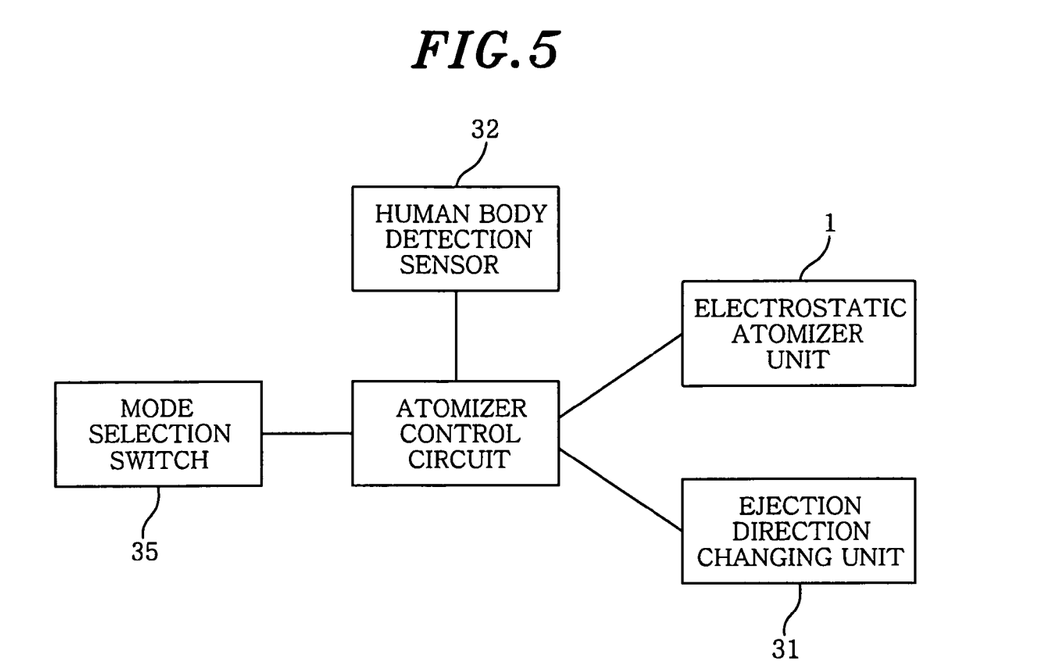

In this regard, the electrostatic atomizer may operate the ejection direction changing unit 31 in two modes, i.e., an ejection direction changing mode in which the ejection direction changing unit 31 is operated to spray the nano-size mist M toward the persons detected by the human body detection sensor 32 and a normal mode in which the nano-size mist M is sprayed downwards without having to change the ejection direction. In this case, the electrostatic atomizer includes a mode selection switch 35 as shown in FIG. 5. The mode selection switch 35 enables a user to select one of the modes mentioned above. This makes it possible for the user to choose an option in which the nano-size mist M is ejected toward the vehicle occupant in an increased amount or an option in which the nano-size mist M is evenly diffused throughout the vehicle room 21.

As the human body detection sensor 32, it is possible to use, e.g., an infrared sensor that detects the person sitting on the seats 22, a weight sensor that detects the weight of a person, a vibration sensor or the like.

The operation of the atomizer unit 1 is governed by an atomizer control circuit. The atomizer control circuit may be connected to a vehicle control circuit C, which governs the operation of individual parts of the motor vehicle 2, so that it can receive various kinds of signals from the vehicle control circuit C. When the motor vehicle 2 is in operation (namely, when an ignition key switch SW is turned on), the atomizer control circuit may receive the signal indicative of the motor vehicle 2 being in operation and may perform the electrostatic atomization work at all times or depending on the output of an odor sensor or an allergen sensor provided within the vehicle room 21.

Figure 8:
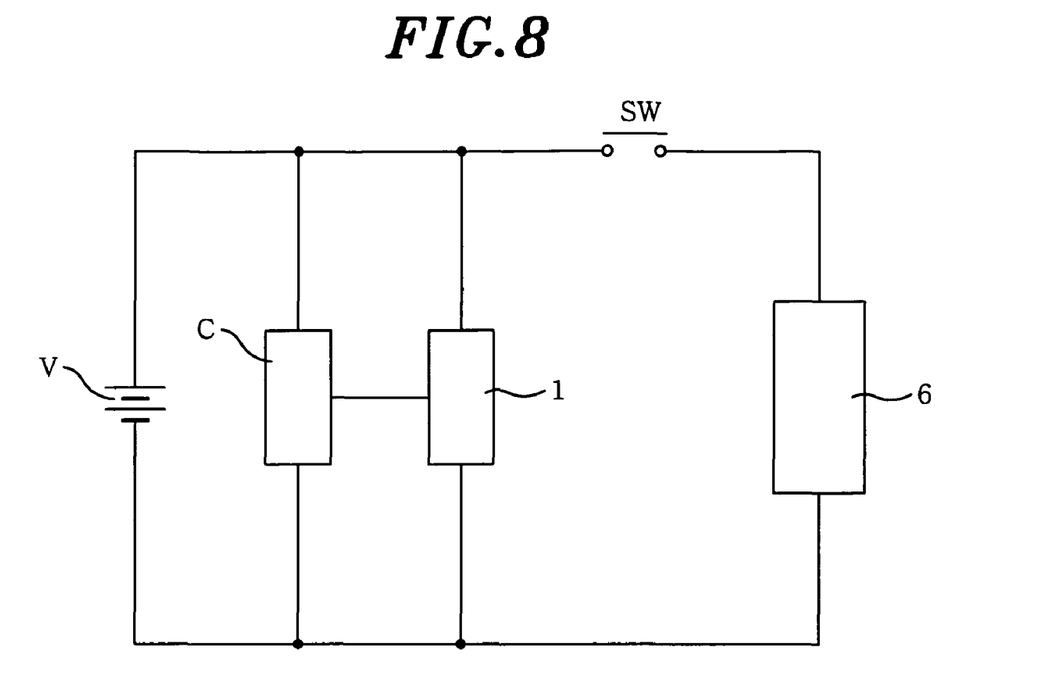

As shown in FIG. 8, the atomizer unit 1 is designed to receive an electric current from a battery V as a power source of the motor vehicle 2 with no intervention of the ignition key switch SW. This makes it possible to perform the electrostatic atomization work even when the ignition key switch SW is turned off. Reference numeral "6" in FIG. 8 designates a vehicle-mounted device.

When the ignition key switch SW is turned off, the atomizer unit 1 begins to perform the electrostatic atomization work when it receives one of the following signals from the vehicle control circuit. More specifically, if the atomizer unit 1 receives a door lock release signal indicative of the locking state of vehicle doors (especially, a driver's seat door) being released or a door lock release command signal outputted upon manipulating a door opening switch 51 of a wireless communication unit 5 of a keyless remote entry system shown in FIGS. 9 and 11, the atomizer unit 1 begins to perform the electrostatic atomization work, i.e., the task of allowing the cooler unit 13 to cool the discharge electrode 11 to produce condensate water and the task of applying a high voltage and inducing electric discharge to generate the nano-size mist M.

Figure 10:
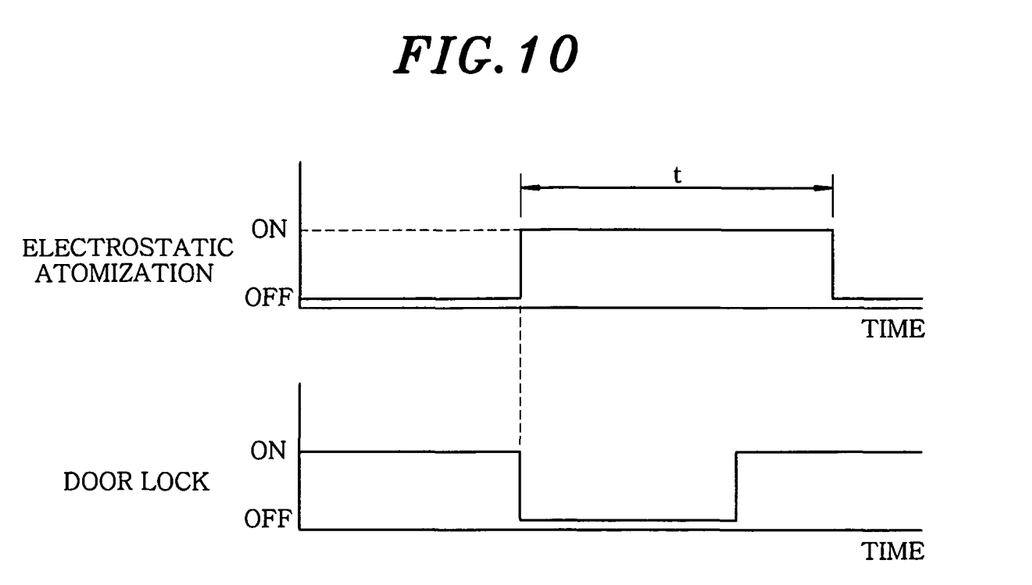

In order to save the electric power of the battery V while an engine is not started up, it is preferred that the atomizer unit 1 is stopped after a predetermined time period has lapsed. It is further preferred that the atomizer unit 1 does not start the electrostatic atomization work when the voltage of the battery V is equal to or lower than a predetermined value. In addition, it is preferred that the electrostatic atomization work started while the engine is not operated continues to be performed for a specified period of time t as illustrated in FIG. 10 even if the doors are locked once again.

In case where the electrostatic atomization work is triggered by the door lock release operation, the nano-size mist M is generated even before the user sits on the driver's seat. Particularly, when the electrostatic atomization work is started by the door lock release command signal supplied from the wireless communication unit 5 of the keyless remote entry system, considerable time is taken until the user opens the door and sits on the seat. The nano-size mist M generated during that period of time can be used in removing odors and inactivating allergens.

The electrostatic atomization work may be triggered not only by the door lock release operation but also by turning on a switch provided to detect whether a key is inserted into the ignition key switch SW.

Figure 9:
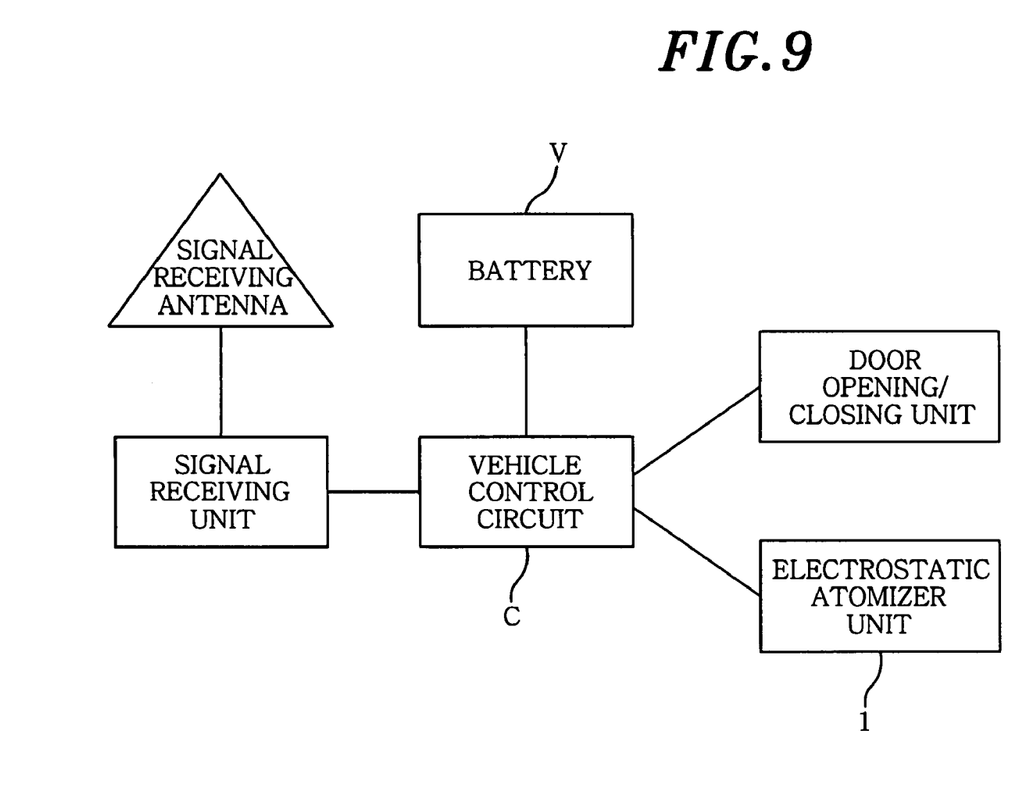
Figure 11:
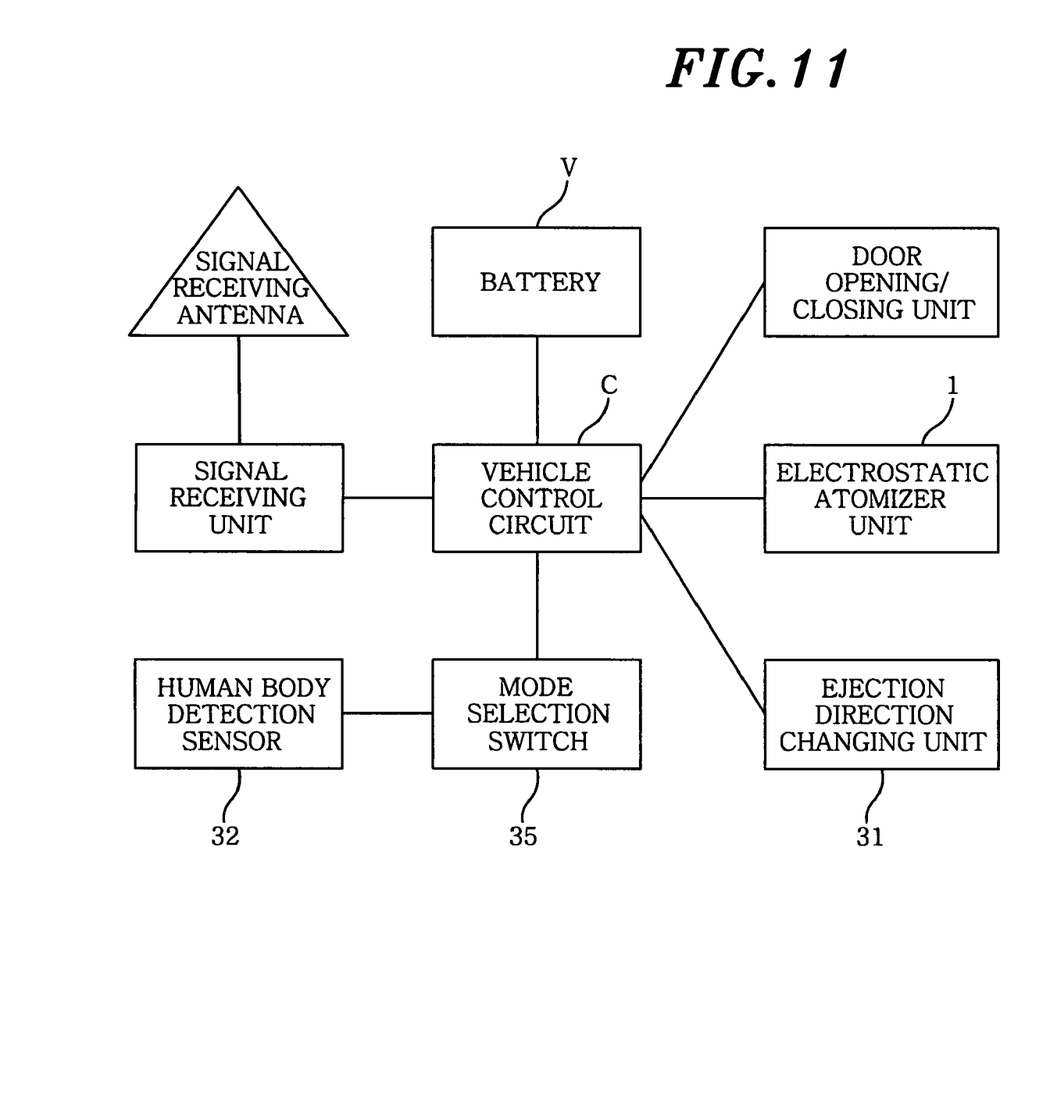

If the odor removal and the allergen inactivation are performed using the nano-size mist M until the user opens the door and gets on the motor vehicle, it is possible to keep the user from suffering from bad odors or allergens at the time of opening the door. Furthermore, it is possible to bring the nano-size mist M into contact with the seat on which the user sits. For that reason, it is particularly desirable to secure time until the door is opened after starting the electrostatic atomization work, namely to start the electrostatic atomization work using the signal sent from the wireless communication unit 5 for keyless remote entry. In addition to the electrostatic atomization work being triggered by the door lock release command signal sent from the wireless communication unit 5, it may be possible to provide an electrostatic atomization switch 53 in the wireless communication unit 5 as shown in FIGS. 9 and 11 so that the electrostatic atomization work can be performed for a specified period of time by turning the electrostatic atomization switch 53 on. The odor removal and the allergen inactivation using the nano-size mist M may be performed when the user leaves the motor vehicle as well as when the user begins to drive the motor vehicle. Reference numeral "52" in FIGS. 9 and 11 designates a door closing switch for issuing a door lock command signal.

While the invention has been shown and described with respect to the embodiments, it will be understood by those skilled in the art that various changes and modification may be made without departing from the scope of the invention as defined in the following claims.

What is claimed is:

1. An electrostatic atomizer mounted in a motor vehicle, comprising:
    an atomizer unit for generating electrically-charged water particles, the atomizer unit including:
        a discharge electrode;
        a water supply unit for cooling the discharge electrode to generate water condensed on the discharge electrode; and
        a high voltage applying unit for applying a high voltage to the water on the discharge electrode to electrostatically atomize the water;
    an ejection portion provided at a ceiling of the motor vehicle for ejecting the electrically-charged water particles generated in the atomizer unit and an ejection direction changing unit provided in the ejection portion for changing an ejection direction of the electrically-charged water particles; and
    a human body detection sensor for detecting one or more vehicle occupants,
    wherein the ejection direction changing unit operates in two modes, the two modes including an ejection direction changing mode and a normal mode for spraying the electrically-charged water particles downwards without changing the ejection direction, and
    wherein, in the ejection direction changing mode, the ejection direction changing unit is configured to direct the electrically-charged water particles only toward the detected vehicle occupants, and when two or more vehicle occupants are detected, the ejection direction changing unit directs the electrically-charged water particles toward the detected two or more vehicle occupants.

2. The electrostatic atomizer of claim 1, wherein, when two or more detected vehicle occupants are detected, the ejection direction changing unit is configured to change the ejection direction of the electrically-charged water particles such that the electrically-charged water particles are ejected only toward the vehicle occupants one after another.

3. The electrostatic atomizer of claim 1, further comprising:
    a mode selection switch for selecting said one of the two modes.

4. The electrostatic atomizer of claim 1, wherein the ejection portion is separated from a conditioned air ejection port of an air conditioner of the motor vehicle.

5. The electrostatic atomizer of claim 1, wherein the human body sensor includes an infrared sensor, a weight sensor, or a vibration sensor.

6. The electrostatic atomizer of claim 1, further comprising:
- an odor sensor for detecting odor, the odor sensor being provided within the motor vehicle; and
- an atomizer control circuit configured to control the atomizer unit such that the atomizer unit starts generating the electrically-charged water particles when the odor is detected by the odor sensor.

7. The electrostatic atomizer of claim 1, further comprising:
- an allergen sensor for detecting allergen, the allergen sensor being provided within the motor vehicle; and
- an atomizer control circuit configured to control the atomizer unit such that the atomizer unit starts generating the electrically-charged water particles when the allergen is detected by the allergen sensor.

8. The electrostatic atomizer of claim 1, further comprising:
- an atomizer control circuit configured to control the atomizer unit such that the atomizer unit starts generating the electrically-charged water particles when the atomizer control circuit receives a door lock release signal which indicates a locking state of a vehicle door being released.

9. The electrostatic atomizer of claim 8, wherein the atomizer unit is configured to receive an electric current from a battery of the motor vehicle as a power source with no intervention of an ignition key switch for starting the motor vehicle so that the atomizer unit is allowed to generate the electrically-charged water particles even when the ignition key switch is turned off.

10. The electrostatic atomizer of claim 9, wherein the atomizer control circuit is configured to control the atomizer unit such that the atomizer unit stops generating the electrically-charged water particles after a predetermined time period has lapsed since the atomizer unit started generating the electrically-charged water particles.

11. The electrostatic atomizer of claim 9, wherein the atomizer control circuit is configured to control the atomizer unit such that the atomizer unit does not start generating the electrically-charged water particles when the voltage of the battery is equal to or lower than a threshold value.

* * * * *